United States Patent [19]

Weston

[11] Patent Number: 4,988,482
[45] Date of Patent: Jan. 29, 1991

[54] METHOD AND APPARATUS FOR CHEMICAL ANALYSIS

[75] Inventor: Terence E. Weston, Woodbridge, England

[73] Assignee: Microvol Limited, Ipswich, England

[21] Appl. No.: 203,086

[22] PCT Filed: Oct. 5, 1987

[86] PCT No.: PCT/GB87/00704
§ 371 Date: Jun. 1, 1988
§ 102(e) Date: Jun. 1, 1988

[87] PCT Pub. No.: WO88/02865
PCT Pub. Date: Apr. 21, 1988

[30] Foreign Application Priority Data

Oct. 7, 1986 [GB] United Kingdom ............... 8624064

[51] Int. Cl.$^5$ .................. G01N 35/00; B01L 3/02
[52] U.S. Cl. ........................ 422/100; 422/63; 422/104
[58] Field of Search .................. 422/63-65, 422/68, 81, 100, 104; 222/135, 144.5, 162, 325, 402.1, 402.2, 402.23, 504

[56] References Cited

U.S. PATENT DOCUMENTS

| 3,952,916 | 4/1976 | Phillips | 222/70 |
| 4,262,711 | 4/1981 | Anderson | 141/238 |
| 4,361,253 | 11/1982 | Flynn et al. | 222/162 |
| 4,675,163 | 6/1987 | Mybeck | 422/100 |
| 4,798,705 | 1/1989 | Jakubowicz | 422/63 |
| 4,818,493 | 4/1989 | Coville et al. | 422/102 |
| 4,844,868 | 7/1989 | Rokugawa | 422/64 |

Primary Examiner—Robert J. Warden
Assistant Examiner—D. John Griffith, Jr.
Attorney, Agent, or Firm—Lee, Mann, Smith, McWilliams & Sweeney

[57] ABSTRACT

Apparatus for performing chemical analysis wherein a cuvette holds a sample under examination and a support carries a dispenser head carrying two one-shot dispensers each in the form of a pressurized container holding a liquid reagent, of which a metered does is delivered into the cuvette through a discharge tube fixed to the dispenser head when the body of the container is displaced relative to said discharge tube.

8 Claims, 3 Drawing Sheets

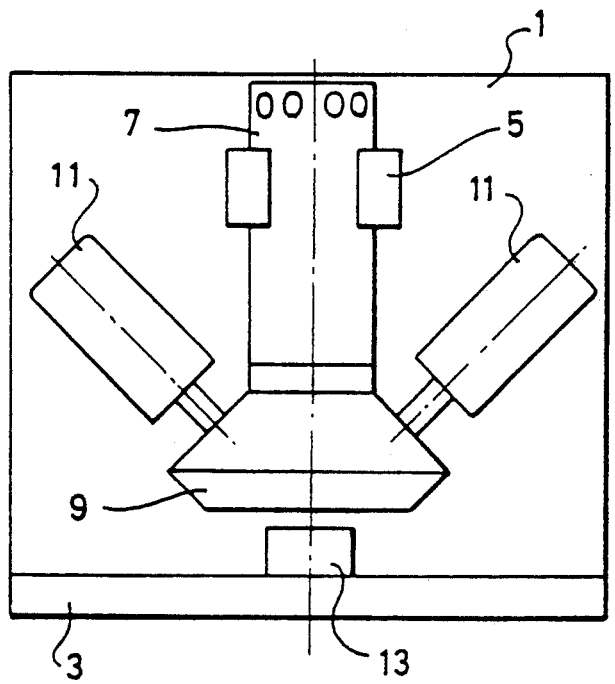
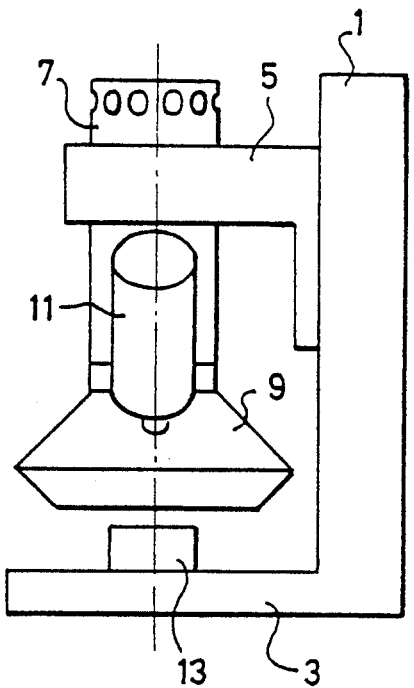
Fig.1  Fig.2
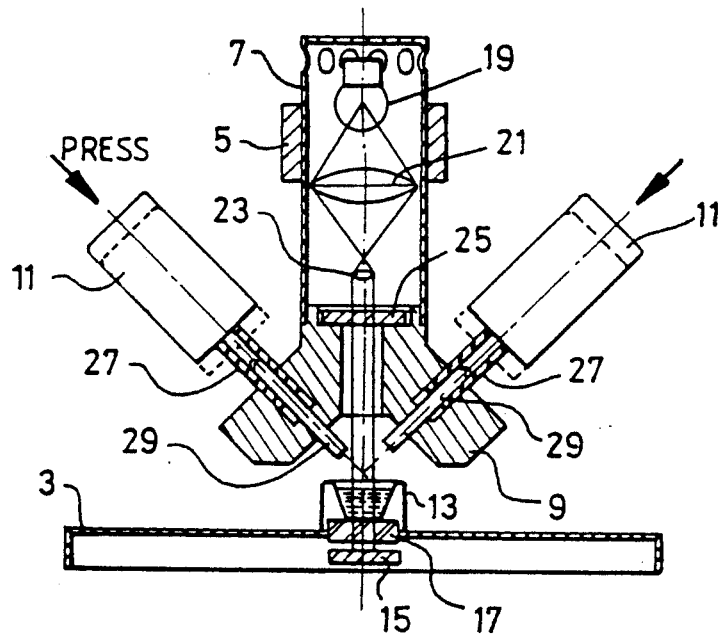
Fig.3

4,988,482

METHOD AND APPARATUS FOR CHEMICAL ANALYSIS

FIELD OF THE INVENTION

The present invention relates to a method and apparatus for chemical analysis and a method and apparatus for dispensing liquid chemical reagents during chemical analysis.

BACKGROUND OF THE INVENTION

Chemical analysis using liquid reagents is widely practiced in many fields, and most especially in medical diagnosis. The term "liquid reagents" encompasses reagents which in their pure or normal state might not be liquid but which have been rendered liquid in some manner such as by dissolving the reagent in a suitable carrier.

Typically, in chemical analysis a sample of the substance to be analysed is placed, sometimes following dilution, in a receptacle commonly known as a cuvette. Measured quantities of one or more liquid reagents are added to the sample in the cuvette and the resulting mixture is then monitored for a change in some selected property. In theory, almost any property could be monitored, but for reasons of practical convenience the property monitored is almost always an optical property. Commonly the mixture will be monitored for a change in colour (i.e. a change in the degree to which one or more specific wavelengths of light are absorbed or transmitted). Other optical properties which may be monitored are turbidity and fluorescence. Non-optical properties which may be monitored are electrical conductivity and pH. In all cases, the chemical reagent or reagents chosen and the property monitored are selected so that the presence or absence of a chemical or type of chemical in the sample can be detected by the presence or absence or the nature of a change in the monitored property of the mixture.

Presently available analytical equipment normally uses peristaltic or piston pumps to deliver the reagents to the cuvette containing the sample. However, these pumps are unreliable and may suffer from leaking seals and split pump tubes. Additionally, the analysers suffer from poor reproducibility of analytical results because the pumps cannot be highly accurate in the quantities of reagents delivered.

A further requirement for accurate analysis is that the liquid reagent should be of good quality and uncontaminated. It is increasingly common for liquid reagents to be pre-packed in bottles which allow improved quality control and security and minimises contamination during storage. When needed, a bottle of a particular reagent is opened and provided as a reservoir for a pump in the analyser apparatus. However, once opened the bottles are subject to contamination if the entire contents of the bottle is not used immediately.

The pumps increase the weight and bulk of the apparatus, and normally need to be driven by motors powered by main electricity. This limits the degree to which such apparatus is portable. Additionally, the pump motors are a source of heat whereas many chemical reagents are heat sensitive. Accordingly, if heat from the pump motors is not to cause deterioration of the reagents the apparatus must be designed to hold the reagent reservoirs or bottles spaced from the pump motors, which tends to increase the size of the instruments and also increases the length of pump tubing which must be employed.

SUMMARY OF THE INVENTION

According to a first aspect of the present invention there is provided a method of dispensing liquid reagents in chemical analysis in which a known volume of reagent is released by the actuation of a 1-shot metering dispenser.

A 1-shot metering dispenser is one in which movement of an actuator from an initial position through an actuating stoke, delivers a single precise volume of liquid and in which no further liquid can be released until the actuating member is allowed to return to its initial position.

Since the dispenser can contain a considerable volume of a reagent it combines the functions of both reservoir and pump, thereby avoiding the need for motor-operated pumps and the like.

Additionally, it is a feature of such dispensers that provided the actuating member travels over the full actuating stroke the quantity of liquid dispensed is determined by the dispenser geometry. Accordingly, the dispenser may be operated manually or by a relatively simple automated mechanism. In either case, the actuating force and/or movement applied to the actuating member need not be precise provided the full stroke length is traversed, yet a precisely metered amount of reagent will be dispensed.

There are two types of 1-shot metering dispenser commonly available.

In the first type, a spring-loaded piston is biased against a first stop and the actuating stroke of the actuating member drives the piston along a cylinder until it is driven against a second stop. The volume dispensed will depend on the swept volume.

In the second type, a pressurized container has an outlet chamber and the container outlet valve is arranged so that when the valve is opened the container pressure dispenses the liquid within the outlet chamber, but no further liquid can then be dispensed until the container outlet valve is closed again. The volume of liquid dispensed is determined by the size of the outlet chamber.

In the case of a spring-loaded piston cylinder dispenser, it is possible to arrange for the container contents to be sealed against the ingress of contaminating material between actuating strokes. In order to prevent contamination of the container contents from air entering the container to replace the dispensed volume of liquid following an actuating stroke, it is possible to provide a sterile and/or chemically inert replacement gas or more preferably the reagent is contained in a flexible and/or collapsible container so that the container volume decreases as reagent is dispensed and no replacement volume of gas is required to enter the container.

In the case of a pressurised container, the container contents are automatically sealed from the surrounding environment when the outlet valve is closed. When the outlet valve is opened the internal container pressure ensures that material can only leave the container and that nothing can enter. In this manner, the container contents are protected from contamination even after the container has begun to be used.

According to a second aspect of the present invention there is provided a method of performing chemical analysis in which a known volume of a liquid reagent is dispensed by the actuation of a 1-shot metering dispenser.

According to a third aspect of the present invention there is provided apparatus for performing chemical analysis comprising: container means to hold a sample to be analysed, support means adapted to receive a 1-shot metering dispenser and support it in a manner allowing relative movement between an actuating member and a further part of the dispenser whereby liquid released by a dispenser in the support means is delivered to the sample holding means when the latter is in a predetermined position, and means for detecting a change in a predetermined property of a sample.

The present invention also provides apparatus in accordance with the immediately preceding paragraph when a 1-shot metering dispenser is located in the support means.

The apparatus may further comprise conveying means to move the container to the predetermined position.

The apparatus may be designed so that reagent released by a dispenser will pass from the dispenser outlet either directly into the sample container or alternatively via a conduit. However, since the need to space the reagent reservoir from the heat of a pump motor does not apply to apparatus embodying the invention, the length of any such conduit will normally be much less than the pump tubing typically employed in conventional apparatus.

It is preferred to use colourimetry to detect changes in the sample (i.e. the sample is monitored for a change in the degree to which one or more specific wavelengths of light are absorbed or transmitted).

It is also preferred to use a 1-shot metering dispenser in which the reagent is stored in a pressurised container.

Accordingly, according to a further aspect of the present invention there is provided a 1-shot pressurised metering dispenser containing a reagent for colourimetry.

Conveniently an inert gas such as argon or nitrogen is employed as the pressurising medium within the dispenser. In contrast to the propellant substances normally used in pressurised containers used for other purposes, such pressurising gases will not normally cause the dispensed charge of liquid reagent to disperse into droplets and form a so-called "aerosol". However it is believed that this does not represent a disadvantage in the dispensing of a liquid reagent in chemical analysis.

The present invention can be applied to sophisticated, high speed and automated apparatus. For example, a large number of dispensers each containing a different reagent may be mounted in a carousel or other storage device and a selected one brought to a dispenser receiving support means for dispensing the reagent into a sample container.

This could be fully powered and automated, with a motorised means to move the actuator through its actuating stroke, all under the control of a computer. Such apparatus may also have an automatic sampler and means to drive a succession of sample containers in turn from the automatic sampler to one or more predetermined positions for receiving reagent and on to a further predetermined position in which the mixture in the sample holding means is monitored for a change in a selected property.

The present invention can also be applied to small portable apparatus in which dispensing may be effected by hand, and there may be only one (or a small number of) dispenser receiving supports. However, such portable apparatus may be arranged so that an operator can exchange reagent dispensers readily and quickly to enable metered doses of several different reagents to be dispensed in turn from a single dispenser receiving support means without significant risk of cross-contamination of the different reagents. Such portable apparatus may also be designed so that the sample holding means remains stationary throughout the analysing process or is moved manually in which event the apparatus need contain no motors and may be suitable for battery operation.

Where an optical property of the mixture in the sample holding means is to be monitored, a light source may be used comprising a radioactive substance (such as tritium) and a fluorescent substance which gives off light in response to radiation from the radioactive substance. Such a light source may be used to provide monochromatic light in place of an electric light, thereby reducing the power requirements. In this way, there can be provided compact apparatus which can be operated in the absence of a main electricity supply and yet which can be used to perform a wide variety of chemical analyses with a high degree of accuracy.

It should be noted that in the present specification the term "light" refers to both visible and invisible electromagnetic radiation.

Embodiments of the present invention, given by way of non-limitative example, will now be described with reference to the accompanying drawings.

BRIEF DESCRIPTION OF THE DRAWINGS

FIG. 1 is a front view of a first apparatus embodying the present invention;

FIG. 2 is a side view of the apparatus of FIG. 1;

FIG. 3 is a vertical section through the apparatus of FIG. 1;

DETAILED DESCRIPTION OF THE ILLUSTRATED EMBODIMENTS

Figure 4:
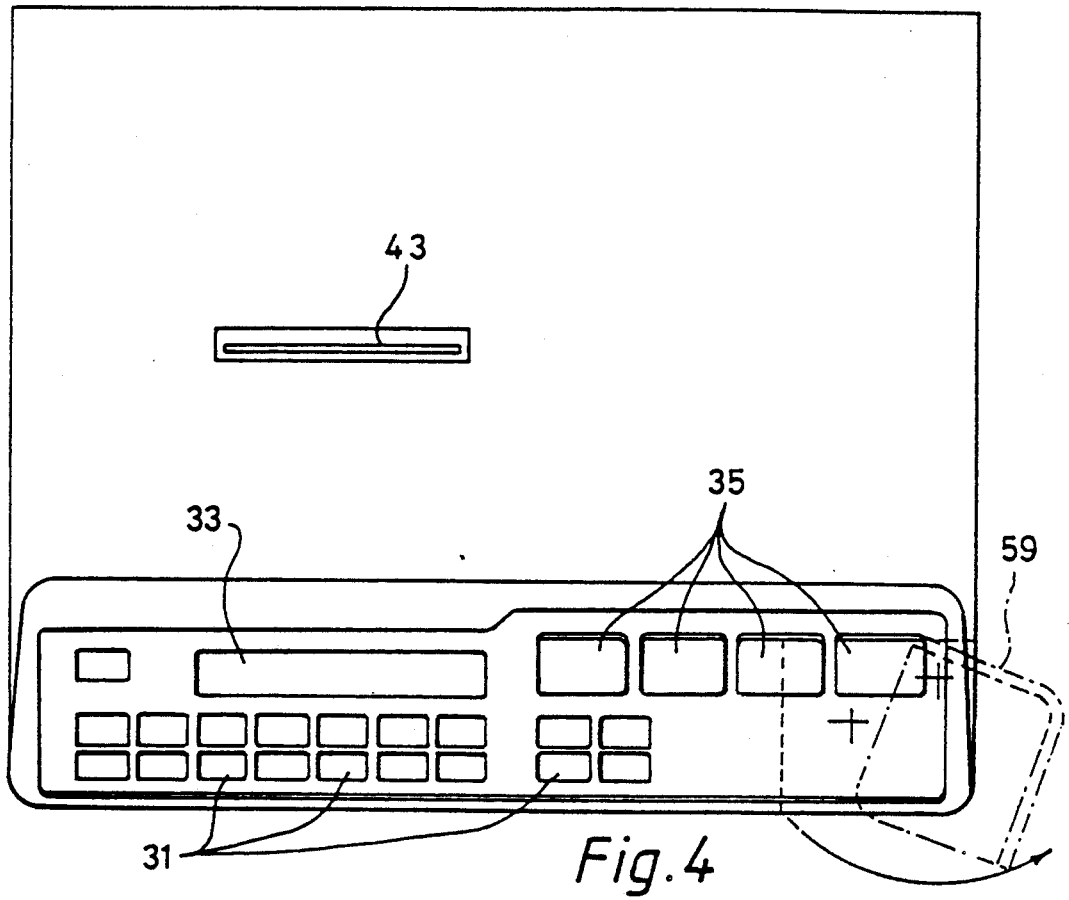
FIG. 4 is a top view of a second apparatus embodying the present invention.

The apparatus illustrated in FIG. 1 has a backplate 1 which extends vertically upwardly from a baseplate 3. Arms 5 extending horizontally from the backplate 1 support a lamp housing 7 and further parts attached to it. The lower end of the lamp housing 7 is attached to a dispenser head 9, which supports two pressurised one-shot dispensers 11. A cuvette 13 is placed on the baseplate 3 beneath the dispensing head 9, and a photodetector 15 is positioned beneath the cuvette. A window 17 in the baseplate 3 protects the photodetector from dirt and damage.

In the lamp housing 7 there is a lamp 19 and a lens system 21, 23. The lens system focusses the light from the lamp 19 into a beam directed towards the cuvette 13 and photodetector 15. The dispensing head 9 has a central vertical aperture to permit this beam to pass through it. At the top of the dispensing head 9 a filter 25 is placed across the beam from the lamp 19, in order to remove wavelengths of light from the beam which are not desired. The cuvette 13 and window 17 are transparent to the wavelength or wavelengths in the filtered light beam which are to be monitored by the photodetector 15.

The dispensing head 9 supports two pressurised dispensers 11 in a partially inverted position. The dispensers 11 are substantially identical to dispensers already known and in use for dispensing one-shot metered doses of pharmaceuticals in aerosol form for use in inhalers for the treatment of asthma and the like. Accordingly, the structure of the dispensers 11 will not be described in detail.

The outer cannister of each dispenser 11 terminates in an outer discharge tube 27. An inner discharge tube 29 is slidable within the outer discharge tube 27, and is biased outwardly. Movement of the inner discharge tube 29 inwardly along the outer discharge tube 27 opens the outlet valve of the dispenser 11 so that the contents of an outlet chamber in the dispenser 11 are discharged through the tubes 27, 29 by the pressure within the dispenser 11 so that the inner discharge tube 29 of each dispenser faces the cuvette 13. The inner discharge tube 29 of each dispenser 11 is restrained from movement towards the cuvette 13, but the main body of each dispenser and the outer discharge tube 27 are slidable relative to the dispensing head 9 towards the cuvette 13. Accordingly, if a dispenser 11 is pushed downwardly and inwardly of the dispensing head 9 towards the cuvette 13 (to reach the position shown in broken lines in FIG. 3) the inner discharge tube 29 of the dispenser will move inwardly of the dispenser relative to the outer discharge tube 27, resulting in the discharge into the cuvette 13 of a metered dose of the contents of the dispenser 11. The dispensers 11 can be removed from the dispensing head 9 by movement upwardly and outwardly, away from the cuvette 13.

In use, the output from the photodetector 15 due to the beam from the lamp 19 is monitored while a measured sample is placed in an empty cuvette 13, which is positioned over the window 17, and metered doses from one or more selected reagents pre-packed in dispensers 11 are added to the sample in the cuvette 13. Changes in the optical properties of the mixture in the cuvette 13 following the addition of the reagent or reagents, is interpreted as indicating the presence or absence of a selected chemical or type of chemical in the sample initially placed in the cuvette 13.

Like the apparatus of FIGS. 1 to 3, the apparatus of FIGS. 4 to 8 uses a photodetector to detect a change in the optical properties of the contents of a cuvette. However, the apparatus of FIGS. 4 to 8 incorporates a microprocessor to assist in interpreting the output of the photodetector.

A sloping front panel of the apparatus of FIG. 4 is provided with keys 31 whereby an operator can input information to the microprocessor and a display 33 for output from the microprocessor. The front panel also has four apertures through which protrude buttons 35 mounted on the ends of pressurised dispensers 37. Thus the operator can cause a metered dose of a reagent in a dispenser 37 to be discharged by pressing firmly on the associated button 35.

The microprocessor also controls a printer 39, so that a written record of the analysis results can be provided. A printer output sheet 41 emerges through a slit aperture 43 in a rearwardly sloping top surface of the apparatus.

Figure 7:
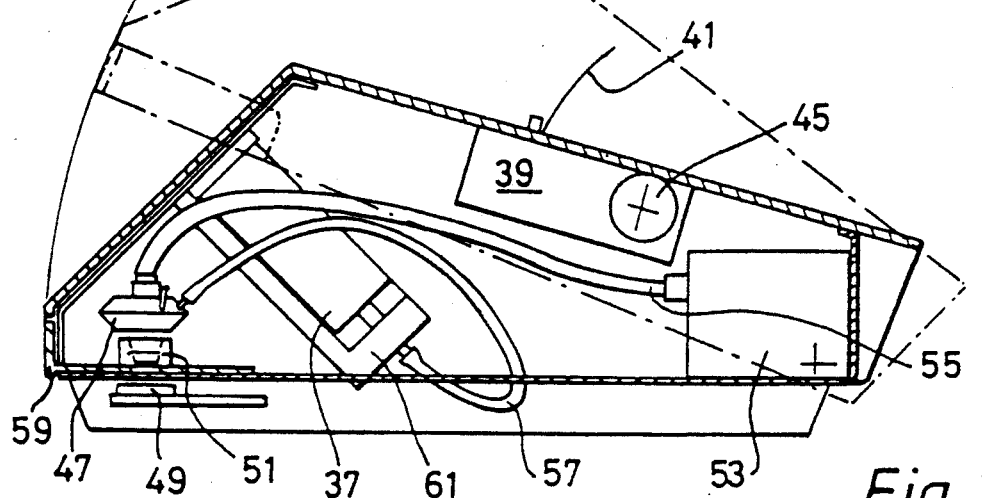
FIG. 7 is a sectional view taken along line A—A in FIG. 5.

An upper portion of the casing of the apparatus, including the sloping front surface and sloping top surface, can be opened upwardly about a hinge at the rear of the apparatus as shown in broken lines in FIG. 7. This provides access to the interior of the apparatus for servicing, and performing such functions as replacing the printer roll 45 and replacing the pressurised dispensers 37.

The apparatus contains a dispensing head 47 which is positioned above a photodetector 49. In use, a cuvette 51 containing a measured sample for analysis is placed between the dispensing head 47 and the photodetector 49. A lamp 53 provides a light beam for use in monitoring the optical properties of the contents of a cuvette 51, and this light beam is conveyed to the dispensing head 47 by an optical fibre 55. The output from the photodetector 49 is provided as an input to the microprocessor, so that the microprocessor can detect changes in the optical properties of the contents of the cuvette 51.

A short length of flexible tubing 57 conveys reagent dispensed from a dispenser 37 to the dispensing head 47.

Although not shown in the drawings, a further optical fibre may carry a further beam from the lamp 53 to a further photodetector. The further beam is provided to the further photodetector without passing through the cuvette 51. The output from the further detector is also provided as an input to the microprocessor. This arrangement provides a comparison or calibration input to the microprocessor, so that the microprocessor can monitor changes in the difference between the outputs of the two photodetectors rather than monitoring solely changes in the output of the photodetector 49. In this way, any changes in the output of the lamp 53 are compensated for automatically.

Figure 5:
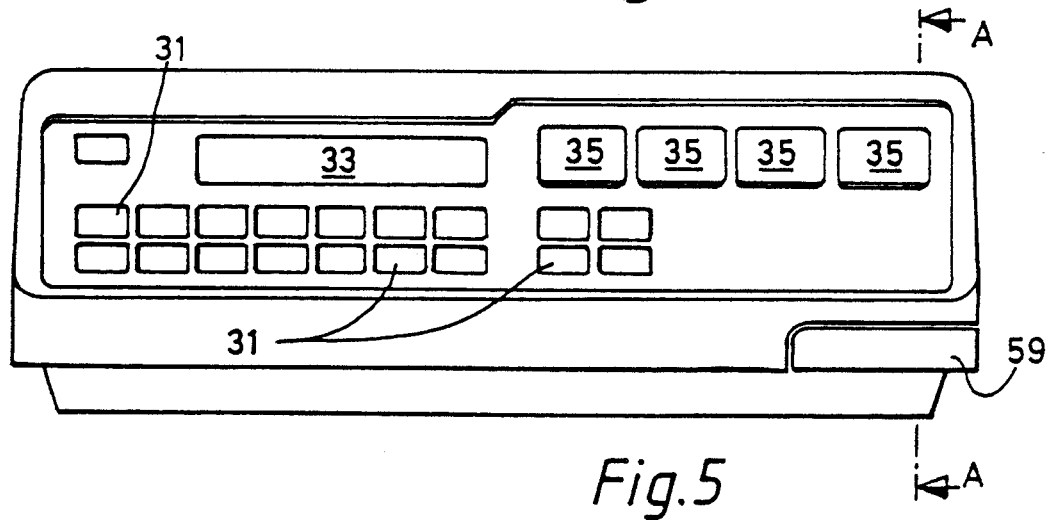
FIG. 5 is a front view of the apparatus of FIG. 4.
Figure 6:
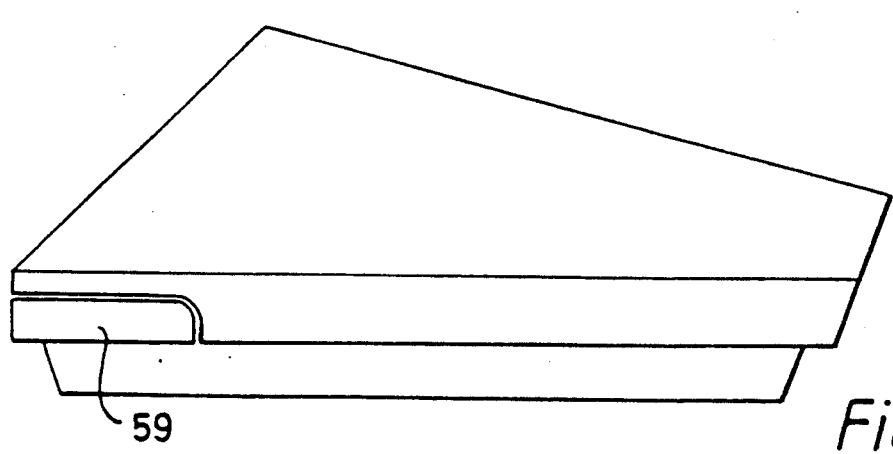
FIG. 6 is a side view of the apparatus of FIG. 4.

At one corner of the apparatus of FIGS. 4 to 8 there is provided a hinged cuvette tray 59. In the normal position of the tray, as shown in FIGS. 5, 6 and 7, a cuvette 51 correctly positioned on the tray 59 is located beneath the dispensing head 47 and aligned with the photodetector 49. From this position, the tray 59 may be swung outwardly of the apparatus about a vertical pivot axis as shown in FIG. 4. The position occupied by the tray 59 part way through its movement is shown in broken lines in FIG. 4.

This movement of the tray 59 carries the cuvette 51 out of the apparatus so that it is accessible to the operator.

In use, the operator swings the cuvette tray 59 outwardly of the apparatus, and places on it a cuvette 51 containing a measured sample for analysis. The operator then swings the tray 59 with the cuvette 51 back into its normal, position. The operator then provides any required input to the microprocessor through the keys 31, and presses a selected pushbutton or pushbuttons 35 in order to discharge into the cuvette 51 a metered dose of a selected reagent or reagents from the dispensers 37. The microprocessor will monitor the output from the photodetector 49, and will compute therefrom the analysis results. These analysis results will then be displayed on the display 33 and/or printed out by the printer 39. When the analysis is finished, the tray 59 is swung outwardly from the apparatus again, and the cuvette 51 removed for emptying and cleaning.

Figure 8:
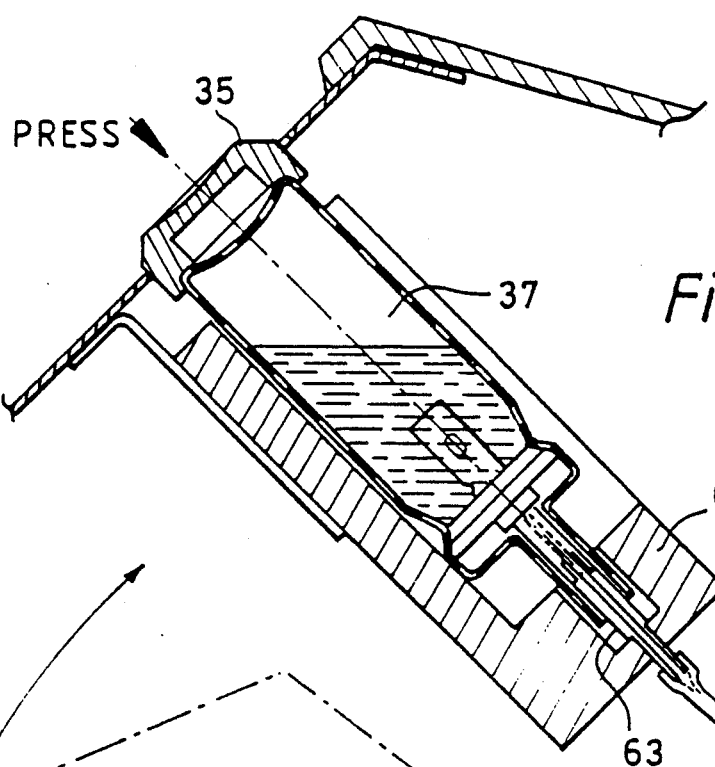
FIG. 8 is a detail from the sectional view of FIG. 7.

FIG. 8 shows a pressurised dispenser 37 in detail, together with its associated pushbutton 35. The dispenser 37 is identical to the dispensers 11 used in the apparatus of FIGS. 1 to 3. The dispenser 37 is supported by a holder 61, which allows the main body of the dispenser 37 to move under pressure from the pushbutton 35, but which restrains movement of an inner discharge tube 63 of the dispenser. Thus the mode of operation of the dispenser 37 of the apparatus of FIGS. 4 to 8 is the same as the mode of operation already described for the dispensers 11 of the apparatus of FIGS. 1 to 3. One end of the flexible tubing 57 is fitted as a push fit on the end of the inner discharge tube 63 of the respective dispenser 37, and the other end of the tubing 57 is fitted as a push fit on a tubing stub on the dispensing head 47. For clarity, FIG. 7 shows only one length of tubing 57, and also shows a second tubing stub on the dispensing head 47 to which a second length of tubing 57 from a second dispenser 37 would be fitted in use.

The apparatus FIGS. 4 to 8 is suitable for use with main electric power or with battery power. In order to relieve the drain on the battery during battery operation, the lamp 53 may be replaced by a light source comprising a radioactive substance and a fluorescent substance which gives off light in response to radiation from the radio active substance. Such a light source does not require any external supply of power.

It should be understood that if desired, an optical focusing system may be provided at the lamp 53 and a filter may be provided in the dispensing head 47 or at the lamp 53, in a manner analogous to the provision of the optical system 21, 23 and the filter 25 in the apparatus of FIGS. 1 to 3.

As will be apparent to those skilled in the art, various modifications are possible to the embodiments described above. For example, a grating monochromator may be used instead of a filter to provide to the cuvette and photodetector light of a suitable wavelength. The detection system of the apparatus may be arranged to detect changes in some other property of the contents of the cuvette, such as fluorescence, refractive index, turbidity of pH. A cam or a solenoid device may be provided to depress the dispensers automatically.

What is claimed:

1. Apparatus for performing chemical analysis comprising in combination:
    sample holding means to hold a sample to be analyzed,
    a 1 shot metering dispenser having a reagent reservoir constantly pressurized by a gas also within said reservoir and a reagent discharge tube,
    support means supporting the dispenser in a manner allowing relative movement between the reservoir and the discharge tube, whereby liquid released by the dispenser is delivered to the sample holding means when the latter is in a predetermined position, and means for detecting a change in a predetermined property of a sample, wherein the reservoir and discharge tube are relatively moveable with unidirectional operating and return strokes to deliver a predetermined amount of reagent from said reservoir to the sample holding means as a result of each operating stroke.

2. Apparatus according to claim 1, further comprising means movably supporting the sample holding means to enable the holding means to be moved to a predetermined position.

3. Apparatus according to claim 1, in which the discharge tube contains a conduit having an outlet disposed adjacent and above the sample holding means in the said predetermined position of said sample holding means.

4. Apparatus according to claim 1, further comprising a storage device for a plurality of said dispensers, whereby a selected dispenser may be brought to the support means for dispensing the liquid contained therein into a sample holding means.

5. Apparatus according to claim 1 in which the dispenser comprises a container containing an inert gas which pressurizes the container.

6. Apparatus according to claim 5, in which the gas is one of nitrogen and argon.

7. Apparatus according to claim 1, in which the means for detecting a change in a predetermined property of the sample is a photodetector which detects an optical property of the sample.

8. Apparatus according to claim 7 in which said photodetector includes means for detecting the color of the sample.

* * * * *